United States Patent [19]

Gotzen et al.

[11] Patent Number: 4,662,365

[45] Date of Patent: May 5, 1987

[54] DEVICE FOR THE EXTERNAL FIXATION OF BONE FRAGMENTS

[75] Inventors: Leo Gotzen, Hanover; Uwe Brudermann, Kiel, both of Fed. Rep. of Germany

[73] Assignee: Ortopedia GmbH, Salzredder, Fed. Rep. of Germany

[21] Appl. No.: 556,845

[22] Filed: Dec. 1, 1983

[30] Foreign Application Priority Data

Dec. 3, 1982 [DE] Fed. Rep. of Germany ....... 3244819

[51] Int. Cl.$^4$ .............................................. A61F 5/04
[52] U.S. Cl. ......................... 128/92 ZW; 128/92 YE; 128/92 Z
[58] Field of Search ............ 128/92 A, 92 R, 92 ZW, 128/92 Z, 92 YE

[56] References Cited

U.S. PATENT DOCUMENTS

| | | | |
|---|---|---|---|
| 1,201,864 | 10/1916 | Overmeyer | 128/82 R |
| 1,960,892 | 5/1934 | Boever | 128/92 A |
| 2,251,209 | 7/1941 | Strader | 128/92 A |
| 2,391,537 | 12/1945 | Anderson | 128/92 A |
| 4,244,360 | 1/1981 | Dohogne | 128/92 A |
| 4,271,832 | 6/1981 | Evans et al. | 128/92 A |
| 4,312,336 | 1/1982 | Daniel et al. | 128/92 A |
| 4,361,144 | 11/1982 | Slätis et al. | 128/92 R |
| 4,393,868 | 7/1983 | Teague | 128/92 A |
| 4,414,966 | 11/1983 | Stednitz | 128/92 A |
| 4,476,865 | 10/1984 | Failla et al. | 128/325 |

FOREIGN PATENT DOCUMENTS

| | | | |
|---|---|---|---|
| 2029702 | 3/1980 | United Kingdom | 128/92 A |
| 2040168 | 8/1980 | United Kingdom | 128/92 A |
| 506405 | 3/1976 | U.S.S.R. | 128/92 A |
| 721090 | 3/1980 | U.S.S.R. | 128/92 A |

Primary Examiner—Gene Mancene
Assistant Examiner—C. W. Shedd
Attorney, Agent, or Firm—Lackenbach Siegel Marzullo & Aronson

[57] ABSTRACT

The device for the external (outside of the patent's body) fixation of bone fragments in the surgical treatment of fractures uses a unitary supporting bar (2) which, particularly in the case of shin-bone fractures, is positioned on the front side with a very close spacing from the bone and, for reasons of X-ray diagnosis, with a slight lateral displacement. A system of basic clamp assemblies (11), compound clamp assemblies (14) and paired clamp assemblies (12, 12a), and the thus facilitated surgical operation techniques, provide for mechanically highly stable fixation of the bone fragments being particularly careful as far as traumatizing is concerned, and being particularly favorable with respect to the psychic and physical restraint to the patient during the period in which the device is applied, and with respect to the cosmetic success upon convalescence. Due to a high degree of standardization, the system of the jaws combines cost-reducing manufacture with uncomplicated surgical operation techniques and with all possibilities for necessary corrective measures; the system favors both careful application and cosmetic success.

13 Claims, 5 Drawing Figures

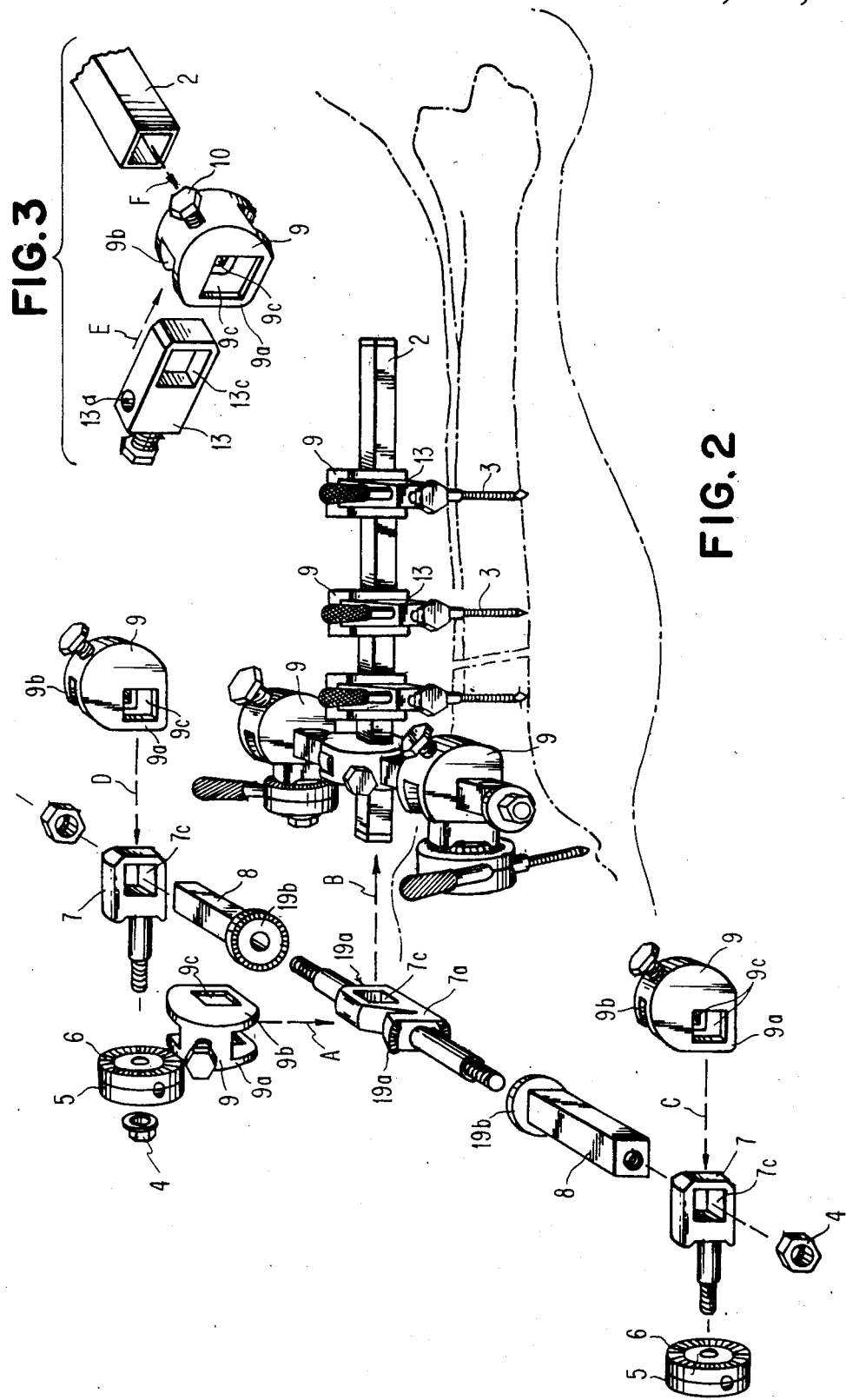

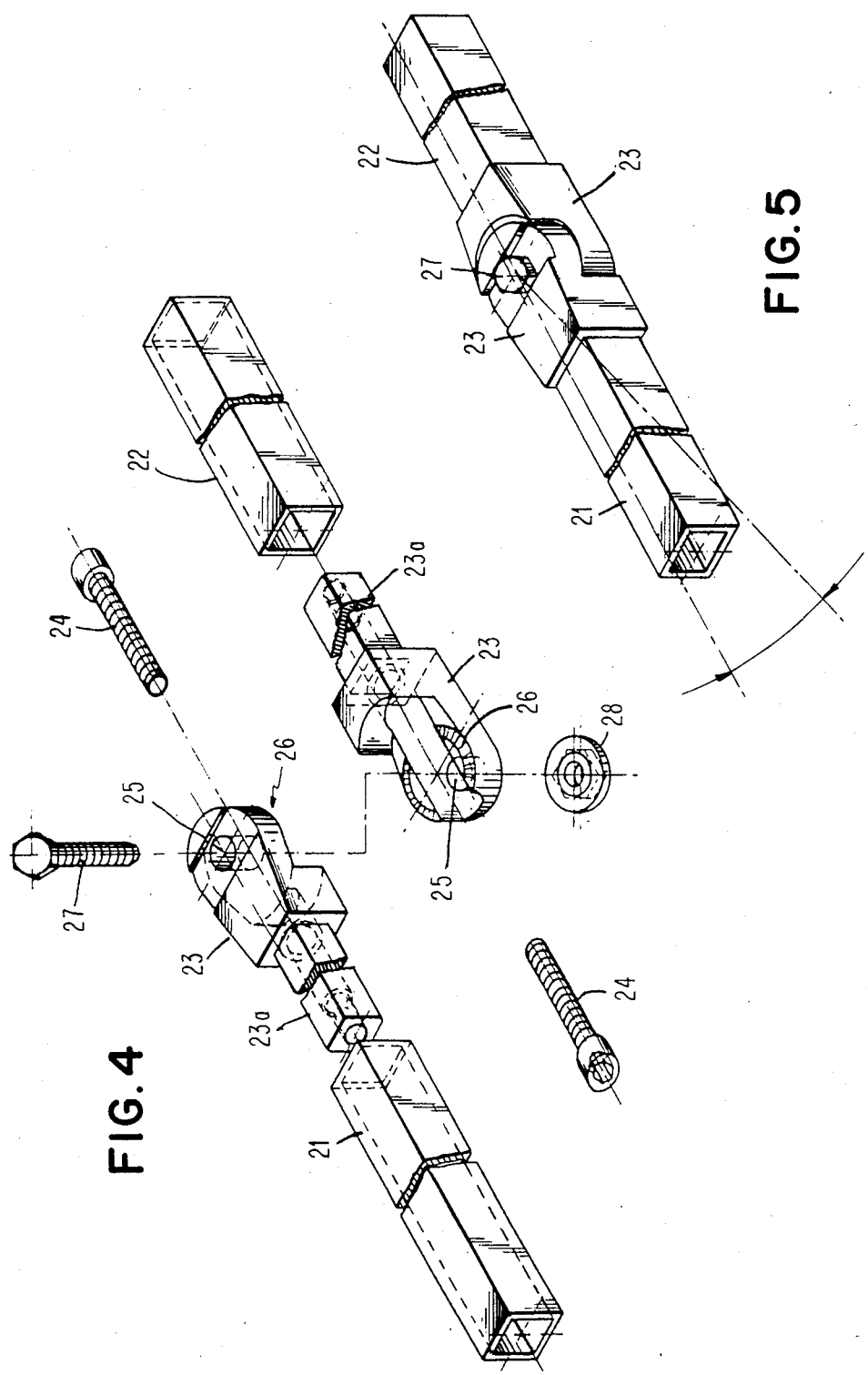

DEVICE FOR THE EXTERNAL FIXATION OF BONE FRAGMENTS

The present invention relates to a device for the external relative fixation of bone fragments, in the form of a frame having brackets for bone pins to be inserted into the respective bone fragments.

Devices of this type are known under the term "Fixateur externe". These devices serve to immobilize bone fragments from the exterior, i.e. with the aid of support means positioned outside of the body, namely to fix the bone fragments against relative movement so as to permit them to grow together after a fracture. Devices of this type are always used in the case of highly complicated, second-degree or third-degree fractures with substantial lesion to fleshy parts, which frequently occur with crural fractures such as, for example, in motorcycle accidents. Essential to healing is in this instance an adequate immobilization of the bone fragments and of the fleshy parts, which at the same time are to be affected by surgical operation to a minimum degree only.

Normally, the accident-surgical treatment of fractures of this kind is effected in such a way that spikes (e.g. Steinmann's spikes) and screws (bolts) (e.g. Schanz's screws) are anchored in the bones transverse to the main direction of extension of the bone, and that these elements are thereafter interconnected through an external frame in order to fix the fragments as rigidly as possible relative to each other to thereby secure the requisite immobilization of the fracture points with respect to each other.

The conventional frame constructions, termed "Fixateur externe", form a relatively voluminous three-dimensional, strange structure in the vicinity of the affected body region (e.g., the so-called tent roof structure). In the conventional constructions, this is necessary in order to obtain sufficient mechanical strength, because a plurality of interconnected support bars or rods, in turn, have to be connected (secured) to the fragments by a relatively great number of spikes and screws from various directions. Frequently, this results in unavoidable extra lesion to bones and soft parts, with the connecting elements, owing to their sharp edges, often causing further injuries.

Accordingly, it is the object of the present invention to provide a device for the external mutual fixation of bone fragments, which device, while having good mechanical stability, requires a minimum of component parts and may be attached to the fractured bone substantially from one side only, but as close as possible to the fractured bone, such that the (size) reduction of the supporting frame also minimizes the risk of additional lesion to soft parts. Further, this device should be constructed from a minimum of different parts, thereby to facilitate assembling on the one hand, and keep the cost low on the other hand.

For achieving this object, the device according to the invention is characterized by a supporting bar having a non-circular cross-section, and at least one pair of clamped jaw assemblies rotatably slid onto the supporting bar and adapted to be moved in the longitudinal direction of the supporting bar and further adapted to be locked by a holder element, said assemblies each having clamping means for securing a bone pin, with said jawed assembly being mounted in a position substantially perpendicular to the supporting bar, and the axes of the bone pins being disposed substantially normal to a plane extending through the supporting bar.

Thus, the fixing device according to the invention comprises as the primary element a single supporting bar to which various clamping assemblies including the respective bone pins may be mounted as required. Unlike the conventional frame structures, the single supporting or mounting bar employed in the invention is adapted to be mounted in a position extremely close to the body, whereby the stability of the fragment fixation is significantly improved because of the close spacing between the bones and the supporting bar. Owing to this structure, the device according to the present invention is also operative with a relatively small number of bone pins, thereby to correspondingly reduce trauma to soft parts and bones, too. Furthermore, this device offers the advantages of substantially improved cosmetics, both during the implantation period due to the small spatial dimensions of the fixing device, and after healing of the fracture and removal of the device due to the small number of bone pins. This is of particular benefit in the treatment of a fractured shin-bone where the supporting bar can be positioned in the ventral region with a particularly close spacing to the body.

Another advantage of the invention resides in the fact that, owing to the jawed clamping and holding assemblies which extend laterally from the supporting rod, upon application of the system to the bone the supporting bar is slightly displaced in lateral direction relative to the position of the bone, in plane view. This permits better diagnosis of the healing process by X-ray examination, because the supporting rod, being impermeable to X-rays, does not conceal the treated bone. A further advantage of the construction according to the invention is that the small number of component parts used therein may be designed to be small in size and rounded, thereby additionally reducing the risk of injury.

A very important advantage of the system is that it enables a dynamic external splinting with neutralization of bending and rotation movements through removal of the locking screws in the fixation clamps on one fracture side.

Special configurations and further developments of the invention are characterized in the dependent claims.

BRIEF DESCRIPTION OF THE DRAWINGS

FIG. 2 is an exploded view of a pair of clamping assemblies (12, 12a) as seen at the top of FIG. 1.

FIG. 3 is a detailed exploded view of a basic clamp assembly (15) as seen near the bottom of FIG. 1.

FIG. 4 is an exploded view of the joinder of two supporting bars (2), herein (21, 22).

FIG. 5 is a perspective view after the joinder of two supporting bars (21, 22).

Figure 1:
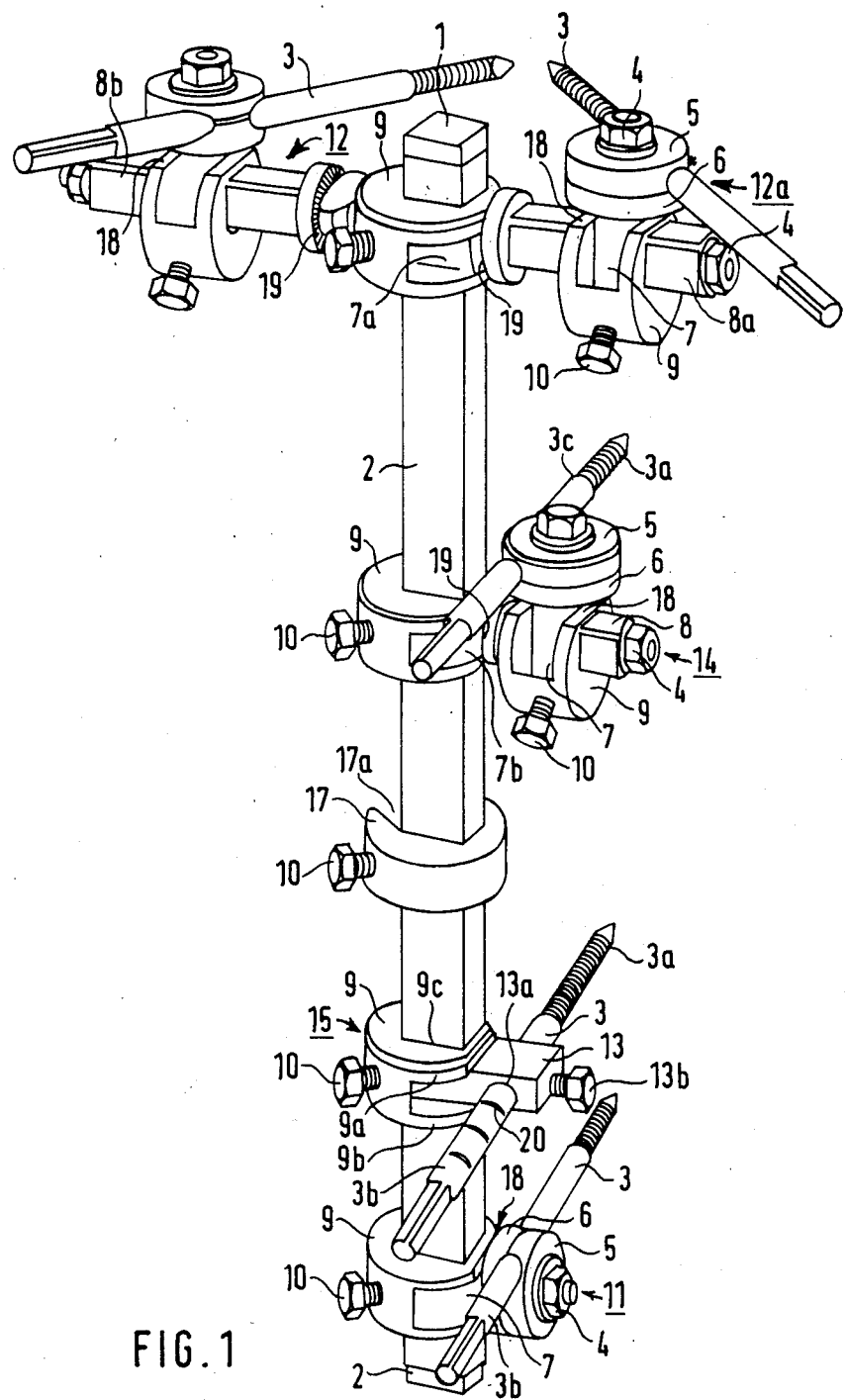
FIG. 1 is a perspective view of an embodiment of the present invention showing a supporting bar and one each of the types of jawed clamp assemblies.

The basic part of the device is a supporting bar 2 formed as a square tube in the embodiment shown, with the ends of the square tube closed by a stopper 1. The supporting bar is formed of a material approved for the surgical field of application according to German Industrial Standards (DIN). Instead of the square profile, it is also possible to use a different noncircular profile which, when correspondingly adapted to the recesses of the jaws, provides for mounting of the various to prevent rotation.

Jawed clamping assemblies of different design may be positioned on the supporting bar 2 to be movable in axial direction and adapted to be locked in the respectively desired positions. The jaws shown are designated in the following specification as standard basic clamp assembly 15, single clamp assembly 11, compound clamp assembly 14, paired clamp assemblies 12 and 12a, and block jawed clamp 17. These different jaws comprise in part identical, uncomplicated basic elements, and extra functions may be obtained with the addition of extra parts.

The various jawed assemblies each include a pin holder 7, 7a, 7b or 13, a forked clamp 9 and a clamping screw 10. Each pin holder 7, 7a, 7b or 13 comprises a solid workpiece having a recess complementary to the square profile of the supporting bar and through which the square profile can slide smoothly. The forked clamp 9 has its two forked ends 9a and 9b likewise provided with aligned recesses 9c adapted to the square profile of the supporting rod. The spacing between the forked ends 9a and 9b provides just sufficient space for receiving the respective pin holder 7, 7a, 7b or 13 which is respectively inserted such that all three recesses, namely those of the two forked ends and that of the pin jaw holder, are aligned with each other, whereby the jaw carrier and the forked clamp may be slipped onto the supporting bar 2 as a unit. Clamping between the parts is effected by the clamping screw (bolt) 10 which extends in the diagonal direction, i.e. in the direction toward one edge of the supporting rod 2; this results in an extremely tight and play-free union between the supporting bar 2, the pin holder 7, 7a, 7b or 13 and the forked clamp 9.

The basic clamp assembly 15 includes only one pin holder 13 which, at the same time, acts as a clamping means for a pin-shaped or screw-shaped bone pin 3. To this end, the pin holder 13 is provided with a receiving hole 13a extending transversely to the longitudinal directions of the jaw carrier and of the supporting bar and into which the bone pin 3 may be inserted to be secured therein by means of a clamping screw 13b. With this uncomplicated basic clamp 15, bone pin 3 may be adjusted along the length of the supporting bar 2, in axial direction relative to the implantate 3 and in a rotatory sense around the axis of the bone pin.

The single clamp assembly 11 includes a pin holder 7 locked to the supporting bar 2 by means of a forked clamp 9 and a clamping screw 10. The clamping means of this single clamp assembly 11 comprises a pair of discs 5 and 6 receiving between them the bone pin 3 in notches and adapted to be clamped against each other by means of a screw or bolt 4. A lock (ratchet-type) plate coupling 18, shown only fragmentarily in FIG. 1, is disposed between the jaw carrier 7 and the clamping means 4, 5 and 6. This lock plate coupling provides for additional rotatory adjustment of the implantate 3 such that the latter may be connected to the supporting bar 2 to be adjustable with four axes of motion.

As further shown, the compound clamp assembly 14 includes a square lug 8 adapted to be locked to the supporting bar 2 with the cradle 9 and the clamping screw 10 by means of a lock plate coupling 18 and a pin holder 7b. A single-clamp assembly 11, as described above, is secured to the square lug 8, namely through a pin holder 7, a cradle 9 and a clamping screw 10. In this compound clamp assembly 14, the implantate 3 is adapted to be adjusted and clamped in all six axes of freedom (directions of movement).

The pair clamp assembly 12 and 12a shown at the upper end of the supporting rod 2 has the function that, for example in the case of a shin-bone fracture, a pair of implantates 3 may be applied approximately at right angle to each other and in coplanar relation approximately normal to the direction of the bone in the vicinity of the joint, without the space required for this structure on the outside of the patient resulting in too much restraint to the patient. In this instance, the component adapted to be adjusted along the supporting bar 2 and comprising a pin holder 7a, a forked clamp 9 and a clamping screw 10 includes one square lug 8a and 8b each on opposite sides. Similarly as in the above-described compound clamp assembly 14, these two square lugs are each clamped relative to the pin holder 7a and the forked clamp 9, respectively, through lock plate couplings 19 including the nuts 4. Further, in the manner described above, single-clamp assembly 11 including the clamping means 4, 5, 6 are respectively mounted on the square lugs 8a and 8b through an associated lock plate coupling 18. Each of the two associated implantates 3 is thus mounted for adjustment in six axes of freedom; however, both implantates are adjustable as a unit along the supporting bar 2.

Finally, a block jawed clamp assembly 17 is also shown. This block jawed clamp assembly comprises a clamp engaging the supporting bar on perhaps three sides and having a clamping screw 10. On the fourth side, the recess 17a is open, permitting the block jawed clamp assembly to be slid onto the supporting bar from one side without the necessity of moving or disassembling the other jaws. Accordingly, the block jawed clamp assembly 17 may be attached to the supporting bar 2 in any free or unoccupied position thereof. This block jaw has the function of forming an abutment, movable along the supporting bar, for operation of customary stretching instruments required for the adjustment of defect distances between the bone fragments or for their compression against each other. In such instance, first the remainder of the longitudinally movable assemblies are released from the supporting bar. Then, the fragments are brought to the desired relative position, and subsequently the remainder of the assemblies are re-clamped to the supporting bar.

Furthermore, for establishing a mechanical connection between a plurality of adjacently positioned bones which were articulated to each other before the fracture, a not illustrated link (joint element) may be provided which is adapted to interconnect a pair of supporting bars through a lockable joint, so as to be adjustable in one axis of freedom.

In the assembling of the fixing device, the implantates mounted in the clamping means 13a, 13b or 4, 5, 6, respectively, may be replaced initially by drilling guides providing for precise orientation of the drill holes to be formed in the bone fragments and being required for securing the implantates. Upon orienting and punch-marking of the drilling position by means of a guide bolt, and after the subsequent drilling of the hole in the bone, the drilling guide is removed, whereupon the then installed implantate is precisely aligned with the drill hole and may be set into the bone.

In the use of the system, it may be generally assumed that the supporting bar 2 alone and four basic clamp assemblies 15 are each required to effect sufficiently precise and stable connection of a pair of fractured elements (fragments). It is only in the case of unfavorable location and configuration of the zone of fracture that other jaws are also required, which are necessary either for a mounting of the implantates differing from the standard case, or which necessitate additional adjustment of the bone fragments upon insertion of the implantates. For proper handling and for universal applicability of the system, the normal surgical instruments are also required in addition to the abovementioned component parts. Expediently, the overall system will be combined within a receptacle adapted to be sterilized, to form a set or kit of implantates, supporting bars, joint elements, jaws, gauges, drills, a torque wrench, the stretching instrument, etc., conformed to the requirements in accident surgery.

Expediently, such implantates 3 are used for the device according to the invention, the threaded end portion 3a of which is of a smaller diameter than that of the remaining portion 3b extending outwards from the bone. These implantates thus have higher flexural strength in the portion externally of the bone, and the step 3c at the end of the threaded part defines a positive stop which provides for improved mechanical connection to the bone and for proper mounting in the bone. Further, this step prevents the bone from being broken by the end of the threaded part when the threads are screwed in to an excessive depth, and by the accompanying gradual increase in core diameter.

As mentioned above, the device according to the invention is not only intended to be of reduced structural dimensions, but also to minimize the risk of injury by avoiding sharp edges. Pursuant to this object, the implantate may be further provided with, for example, notches 20 formed in the region between the portion clamped in the clamping means 13a, 13b or 4, 5, 6, respectively, and the outer end of the respective implantate. With the aid of these notches, the end portion protruding beyond the clamping means may be removed by being broken off or cut off upon completion of the mounting or assembling of the fixing device. Thereupon, the sharp-edged cutting face may be secured by means of corresponding covering caps.

Furthermore, in the device according to the invention, the risk of injury by sharp edges is substantially eliminated since the component parts of the jaws, such as, for instance, the cradles 9 or the clamping means 4, 5, 6, are generally cylindrical in shape and have rounded edges or corners. Similarly, the other edges of the supporting bar or of the jaw elements are likewise rounded.

FIG. 2 shows a fixation device according to the present invention in place with a broken bone and, in addition, an exploded view of the bridging jaw 12 and 12a at the left end of supporting rod 2 (corresponding to the upper end of FIG. 1). FIG. 2 depicts jaw carriers 7 and 7a. The jaw carrier 7b shown in FIG. 1 has the same shape as carrier 7. In FIG. 2, are depicted recesses or holes 7c which are complementary to the square profile of the supporting bar 2 and square lug 8, respectively.

Further in FIG. 2 there is depicted cradle-or fork-line piece 9 having two forked ends 9a and 9b provided with aligned recesses 9c, adapted to receive the square profile of supporting rod 2 or square lug 8.

For assembling the connector, one cradle or fork piece 9 is fitted over the jaw carrier 7a (as indicated by arrow A) and then, the jaw carrier 7a together with cradle 9 is fitted over the supporting bar 2 (arrow B). In a similar manner, cradle pieces 9 together with jaw carriers 7 are fitted over square lugs 8 along the direction of arrows C and D.

FIG. 2 shows also lock plate coupling 19 in an exploded view, composed of lock plates 19a and 19b.

The shape of jaw carrier 13 is depicted in FIG. 3. For mounting this carrier, a cradle is used in a similar manner as described above.

FIG. 4 shows first supporting bar 21 and second supporting bar 22 interconnected at one end 21a and 22a, respectively, and fixed at a desired angle. For this purpose, each of the first and second supporting bars 21 and 22 are provided with a joint member 23, having an edge joint piece 23a to be inserted into hollow supporting bar 21 and 22, respectively, and fixed therein by means of respective cocking screws 24. Each of the joint members 23 is provided with a screw hole 25 and a toothed surface 26. After assembling the two joint members 23 by superimposing the toothed surfaces 26 of the two joint members 23, the through-holes 25 are aligned with each ohter, and a bolt 27 inserted into both through-holes 25.

First and second supporting bars 21 and 22 can be set at any desired angle by rotation about their common axis of bolt 27 and can be fixed at that set angle by tightening nut 28 on bolt 27.

We claim:
1. A device for external fixing of bone fragments by holding bone pins inserted into the bone fragments comprising:
  (a) at least one supporting bar having a non-circular cross-section;
  (b) at least two clamp assemblies non-rotatably slid onto a supporting bar adapted to be moved along a supporting bar and further adapted to be locked in place along a supporting bar, said clamp assemblies selected from the group consisting of basic clamp assembly, single clamp assembly, compound clamp assembly, paired clamp assembly and block jawed clamp;
  (c) said clamp assemblies having a forked clamp for clamping onto a bone pin holder;
  (d) said forked clamps having aligned recesses adapted to the cross-section of the supporting bar and having clamps conforming to the thickness of a bone pin holder and set screw means in the wall interconnecting the clamping forks;
  (e) said bone pin holders having adjustable clamping means for holding bone pins at an adjustable distance from, and at least one adjustable angle from, a supporting bar;
whereby the bone pins hold the bone fragments in an axis approximately parallel to the axis of the supporting bar.

2. A device according to claim 1, wherein the supporting bars (2) are formed as a square tube.

3. A device according to claim 1, wherein the clamping means of the bone pin holder comprises a threaded receiving hole and a set screw therein.

4. A device according to claim 3 wherein a lock plate coupling (19) having an axis of rotation parallel with the supporting bar (2) is provided between the bone pin holder (7a, 7b) mounted to the supporting bar (2) and the clamping means (4, 5, 6).

5. A device according to claim 3, wherein the paired clamp assembly (12, 12a) mounted on the supporting bar (2) comprises a forked clamp (7a, 9) adjustably holding a pair of bone pin holders each having mounted thereon clamping means (4, 5, 6) for a bone pin (3) through a pair of lock plate couplings (18, 19) with mutually perpendicular axes of rotation, whereby the pair of bone pins (3) is set at an arbitrary angle to each other.

6. The device according to claim 5, wherein one half of the paired clamp assembly (12a) comprises a bone pin holder (7a) and the other half (12) comprises a forked clamp (9) attached through a lock plate coupling (18, 19).

7. A device according to claim 3, wherein a blocked jaw clamp (17) is provided which is adapted to the cross-section of the supporting bar (2) and open on one side thereof and adapted to be locked onto the supporting bar by clamping means.

8. A device according to claim 3, wherein the forked clamps (9) and the clamping means (4, 5, 6) are formed with a substantially cylindrical configuration and with rounded edges and corners.

9. A device according to claim 3, wherein a second supporting bar is provided, and both supporting bars are interconnected through a joint fixed at an angle.

10. A device according to claim 3, wherein the clamping means (13a, 13b; 4, 5, 6) are adapted to receive drilling guide bushings.

11. A device according to claim 3, wherein the bone pins (3) have a threaded section on one end and are notched on the opposite end (3b).

12. A device according to claim 3, wherein the bone pins (3) have a threaded end section (3a) with a smaller diameter than the remaining section (3b), whereby a step (3c) is defined at the junction of the threaded section and the thicker section.

13. A device according to claim 1, characterized by a ratchet-type lock plate coupling (19) having an axis of rotation perpendicular provided between the pin holder (7, 7a, 7b) and the clamping means (4, 5, 6).

* * * * *

UNITED STATES PATENT AND TRADEMARK OFFICE
CERTIFICATE OF CORRECTION

PATENT NO. : 4,662,365
DATED : May 5, 1987
INVENTOR(S) : Leo Gotzen and Uwe Brudermann It is certified that error appears in the above—identified patent and that said Letters Patent is hereby corrected as shown below:

In item [73] on the cover page of the patent, change the German word "Salzredder" to -- Kiel --.

Signed and Sealed this

Tenth Day of November, 1987

Attest:

DONALD J. QUIGG

*Attesting Officer*  *Commissioner of Patents and Trademarks*